United States Patent [19]

Westip

[11] 4,215,684
[45] Aug. 5, 1980

[54] PERMANENT ELASTIC NET-SHAPED BANDAGE, ESPECIALLY FOR MEDICAL PURPOSES

[75] Inventor: Wilhelm Westip, Wuppertal, Fed. Rep. of Germany

[73] Assignee: Lohmann GmbH & Co. KG, Neuwied, Fed. Rep. of Germany

[21] Appl. No.: 943,482

[22] Filed: Sep. 18, 1978

[51] Int. Cl.$^2$ ............................ A61L 15/01; D04B 21/00
[52] U.S. Cl. .......................................... 128/156; 66/193
[58] Field of Search .............................. 128/155–158, 128/160, 165, 166, 166.5, 169, 170; 66/169–171, 190, 192, 193, 195

[56] References Cited

U.S. PATENT DOCUMENTS

| | | | |
|---|---|---|---|
| 3,258,941 | 7/1966 | Formenti | 66/193 |
| 3,448,595 | 6/1969 | Baltzer et al. | 128/156 |
| 3,570,482 | 3/1971 | Emoto et al. | 128/156 |

FOREIGN PATENT DOCUMENTS 1352041  5/1974  United Kingdom ................ 128/156

OTHER PUBLICATIONS

*Knitting Dictionary*, p. 79, "Powernet", Jun. 1967.

*Primary Examiner*—C. Fred Rosenbaum
*Attorney, Agent, or Firm*—Becker & Becker, Inc.

[57] ABSTRACT

A permanent elastic net-shaped bandage including a fabric with elastic threads as warps and with non-elastic threads transverse thereto forming wefts. More specifically, the warps are designed as fringe warps of non-elastic threads and are independent of each other while being backed by an elastic synthetic thread. The non-elastic wefts always rest on the same spot of the fringe warp which is engaged by the adjacent weft and between the skips from fringe warp to fringe warp are in an arc-shaped manner lying a plurality of times on the fringe warp.

5 Claims, 1 Drawing Figure

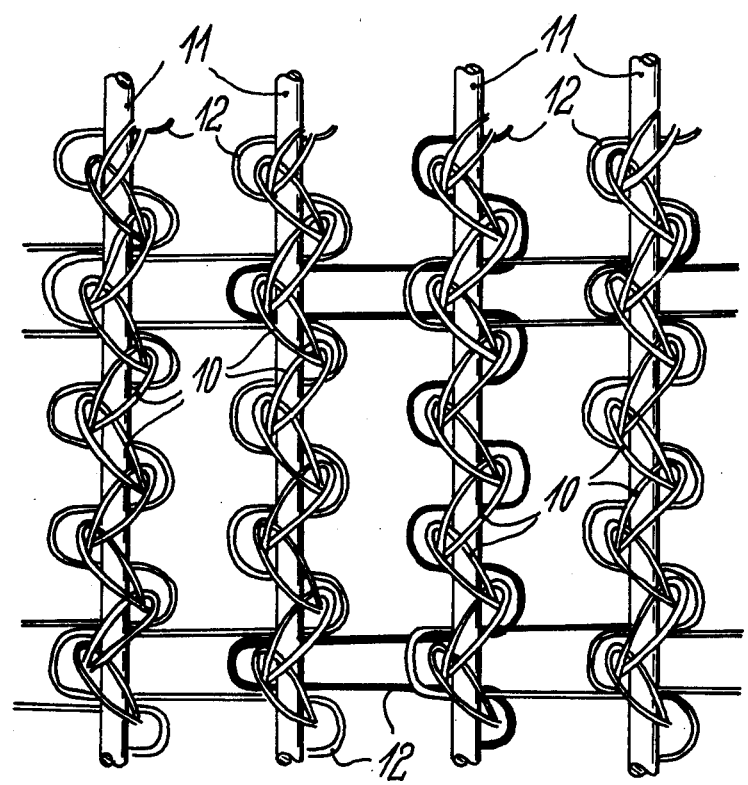

PERMANENT ELASTIC NET-SHAPED BANDAGE, ESPECIALLY FOR MEDICAL PURPOSES

The present invention relates to a permanent elastic bandage with network structure, especially for medical purposes, which comprises a fabric with elastic threads as warps and with wefts extending transverse to said warps and comprising nonelastic threads.

With elastic bandages of the above mentioned type comprising cotton warps, or ideal bandages, the stretching ability is obtained by overtwisted yarns in the direction of the warps, which are placed in the system 2Z, 2S. The stretchability is adjustable by the number of warps. This bandage has the drawback that it has a limited resiliency, in other words, restoring force. This means that the overtwisted yarns (crepe yarns) are so stretched that the bandage after being used over a certain period loses its elasticity. This elasticity can be regenerated only partially by washing.

It is further known, instead of the overtwisted crepe yarns, in the direction of the warps to provide crimp threads of polyamide. The stretching ability of this bandage can be adjusted to about from 60 to 200%. In view of its permanent crimping of the polyamide threads, the bandage has a good restoring capability. By washing such bandage, a complete regeneration of the bandage can be obtained. A drawback of this bandage consists in that considerable heat accumulation is generated when wearing the bandage.

According to another group of heretofore known elastic bandages, the warps are formed of rubber or polyurethane or a combination of these thread types. These bandages have a very good returning capability or elasticity and can well be washed. The density of the threads in such bandages must be so selected that a thread displacement during the use of the bandage will be avoided.

As a result thereof, the bandage is relatively heavy and thick and the wearing comfort is greatly affected thereby.

Other elastic bandages are produced by machine knitting, and in their longitudinal direction have synthetic crimped threads or fibers which have an artificial elasticity.

Moreover, in the longitudinal direction, also non-stretchable threads or fibers, especially cotton threads, are employed. These threads in an alternating manner form parallelly extending warps while the elastic threads are during the warping stretched to a maximum extent, whereas the cotton threads or other non-stretchable threads are processed without stretching or only within normally stretched conditions, so that after the manufacture and the elastic contraction of the synthetic threads, a slackening of the meshes occurs as a result of which the non-stretchable threads form undulations or corrugations. In the transverse direction to these threads, non-stretchable threads are intermeshed or interconnected whereby a meshed bandage is formed. Such bandage obtains its form elasticity due to the fact that at the rim edges, preferably stretchable synthetic threads are inserted. This mesh bandage has a noticeably improved absorption capability. It is very dense and warm and in view of the upsetting or buckling of the non-elastic longitudinal threads has a thick and voluminous appearance. These netted bandages have the drawback that they greatly shrink in width when they extend longitudinally, and that they may cause a heat accumulation.

With the permanent elastic bandage of a network structure as set forth above, between rubber elastic warps, non-elastic wefts are so arranged that the wefts between a first and a second warp engage at another spot on the second warp than do the wefts between the second and a third warp. During a stretching, in this connection a honeycomb shaped deformation is obtained which in response to a unilateral pull only, brings about a shrinking of the fabric transverse to the pulling direction. This shrinking in width affects the uniform engagement of or contact with the body part to be bandaged which likewise is considered a material drawback.

It is, therefore, an object of the present invention to provide a bandage of a network structure, which will be particularly light and large meshed but which will simultaneously eliminate the danger of shrinking in width.

These and other objects and advantages of the invention will appear more clearly from the following specification in connection with the accompanying drawing diagrammatically illustrating the formation of the meshes of an embodiment of a permanent elastic bandage of network structure.

The bandage according to the present invention comprising a fabric with elastic threads as warps and with non-elastic threads transverse thereto as wefts, is characterized primarily in that as warps there are provided fringe warps of non-elastic threads which are independent of each other and which are faced or reinforced by an elastic synthetic thread, and is furthermore characterized in that the non-elastic wefts always engage or rest on the same area of the fringe warp which area is also engaged by the adjacent weft, said non-elastic wefts being between the strips from fringe warp to fringe warp deposited thereon several times in an arc-shaped manner.

Such bandage is well suited for general application as supporting or compression bandage or for use in connection with varicose veins and open sores in combination with a compress. In view of the periodically passing weft lines, the bandage has a considerable lateral and longitudinal stability. The bandage is strong, even though it is light, and has large meshes. Nevertheless, in view of the fact that the wefts engage always the same area of the fringe warp, a shrinking in width is eliminated.

The fringe elements of the longitudinal and machine running direction consist of polyamide threads and are reinforced by elastic threads of rubber or polyurethane alone or in a mixture with other insertable synthetic threads, and more specifically, in such a way that the fringe elements and the elastic threads are placed parallel to each other in certain sections. For forming meshes, these fringe elements and elastic threads are interconnected by the weft which extends perpendicular to the machine direction. The weft changes either to an adjacent fringe or skips one or more fringe elements, then with the next weft returns and is deposited a plurality of times on the same elastic warp.

By means of the weft extending from fringe element to fringe element, the bandage is connected to form a fabric. The short deposit of the weft upon the same warp creates the network-like large mesh appearance of the bandage. Moreover, in this way a wide stable fabric is obtained which in stretched condition has no shrinkage in width. Depending on whether the skip of the weft reaches from one warp to the adjacent warp or farther, a different mesh picture is created without, however, thereby in any way affecting the action of the bandage.

Inasmuch as the knitted-in wefts as for instance cotton, usually have an absorptive capacity, the network shaped bandage can absorb sufficient moisture and thus simultaneously avoids an accumulation of moisture.

Referring now to the drawing in detail, the mesh picture shown therein comprises fringe forming threads 10, for instance of polyamide. With this embodiment, the threads 10 are reinforced with polyurethane threads 11 in stretched condition. Between these fringe forming threads 10 arranged in parallel relationship to each other and extending in the machine running direction, and the polyurethane threads 11, elastic threads 12 such as cotton threads are so shuttled in or picked that the threads 12 will extend uniformly to the adjacent or further remote fringe elements. One of the threads 12 is shown in extended condition in order to more clearly show the course of the thread. In this way, a symmetrical mesh picture is created. This brings about that a shrinkage in width is avoided because the pulling force of the wefts are distributed over the entire surface, are respectively started at the same point, and extend at a right angle to the fringe forming threads or warps 10.

The magnitude of the meshes of the network shaped bandage is dependent on the number of the patterns of a fringe warp 10 and on the distance between the fringe warps 10. The non-elastic weft may also be arranged in a different way. Thus, the weft may change toward the adjacent fringe, may there produce some patterns on the same fringe, and may then again return in order also here to produce a few short arc-shaped patterns. In this connection, the weft always works only one way and not back and forth. The weft may, however, in this way work toward the adjacent fringe and back but will then not produce some arc-shaped patterns but will work like the elastic polyurethane thread and will thus be looped around by the fringe.

It is, of course, to be understood that the present invention is, by no means, limited to the specific showing in the drawing, but also comprises any modifications within the scope of the appended claims.

What I claim is:

1. A permanent elastic net-shaped bandage for medical purposes, comprising a fabric with elastic threads as warps and with non-elastic threads extending transverse thereto and forming wefts, which includes in combination therewith: fringe warps independent of each other and formed by non-elastic threads, and backings of elastic synthetic threads backing said fringe warps, said fringe warps and said elastic synthetic threads being arranged substantially parallel to each other, said non-elastic weft threads and the respective adjacent wefts engaging the same area of the pertaining fringe warp while said non-elastic weft threads between skips from fringe warp to fringe warp are lying on the respective fringe warp in the form of a plurality of arcs, and said pertaining weft threads extending at a substantially right angle to said fringe warps and said elastic synthetic threads.

2. A bandage in combination according to claim 1, in which said wefts skip from one fringe warp to the respective adjacent fringe warp.

3. A bandage in combination according to claim 1, in which said wefts skip from one fringe warp to a remote warp.

4. A bandage in combination according to claim 1, in which the mesh size corresponds to the number of contact areas of said wefts with a fringe warp.

5. A bandage in combination to claim 1, in which the mesh size is in conformity with the distance between two adjacent fringe warps.

* * * * *

UNITED STATES PATENT AND TRADEMARK OFFICE
CERTIFICATE OF CORRECTION

PATENT NO. : 4,215,684
DATED : August 5, 1980
INVENTOR(S) : WILHELM WESTIP

It is certified that error appears in the above—identified patent and that said Letters Patent is hereby corrected as shown below:

On the title page the following should be added:

[30]  Foreign Application Priority Data

Sept. 16, 1977 [DE] Fed. Rep. of Germany ... 2741826

Signed and Sealed this

Eighteenth Day of November 1980

[SEAL]

*Attest:*

SIDNEY A. DIAMOND

*Attesting Officer*  *Commissioner of Patents and Trademarks*

UNITED STATES PATENT AND TRADEMARK OFFICE
CERTIFICATE OF CORRECTION

PATENT NO. : 4,215,684
DATED : August 5, 1980
INVENTOR(S) : Wilhelm Westip

It is certified that error appears in the above—identified patent and that said Letters Patent is hereby corrected as shown below:

Column 3, Line 17, cancel "elastic" and insert
-- non-elastic --.

Signed and Sealed this

Tenth Day of February 1981

[SEAL]

Attest:

RENE D. TEGTMEYER

Attesting Officer

Acting Commissioner of Patents and Trademarks